United States Patent [19]

Pihlaja

[11] Patent Number: 4,649,735

[45] Date of Patent: Mar. 17, 1987

[54] TEST DEVICE AND METHOD FOR TESTING FOAM MATERIAL

[75] Inventor: Roger K. Pihlaja, Sanford, Mich.

[73] Assignee: The Dow Chemical Company, Midland, Mich.

[21] Appl. No.: 796,343

[22] Filed: Nov. 8, 1985

[51] Int. Cl.$^4$ .............................................. G01N 3/30
[52] U.S. Cl. ........................................... 73/12; 73/82
[58] Field of Search ...................... 73/12, 82, 790, 811, 73/813, 818, 823

[56] References Cited

U.S. PATENT DOCUMENTS

| | | |
|---|---|---|
| 3,266,289 | 8/1966 | Stamy . |
| 3,435,658 | 4/1969 | Arthur ................................. 73/82 X |
| 3,453,862 | 7/1969 | Elliott et al. . |
| 3,498,117 | 3/1970 | Dalrymple . |
| 3,576,127 | 4/1971 | Weitzel . |
| 3,724,260 | 4/1973 | Bole . |
| 3,791,193 | 2/1974 | Bole . |
| 3,871,208 | 3/1975 | Berg . |
| 3,896,657 | 7/1975 | Brandt et al. . |
| 4,085,609 | 4/1978 | Kelly . |
| 4,313,337 | 2/1982 | Myint . |
| 4,470,293 | 9/1984 | Redmon ................................. 73/12 |

FOREIGN PATENT DOCUMENTS 1104953 3/1968 United Kingdom .................... 73/12

OTHER PUBLICATIONS

Wnuk et al., "Design and Application of an Instrumented Falling Weight Impact Tester" Polymer--Engr'g & Science, vol. 21, No. 6, Apr. 1981, pp. 313-324.

*Primary Examiner*—Charles A. Ruehl
*Attorney, Agent, or Firm*—B. M. Kanuch

[57] ABSTRACT

A device for testing a sample of foam material and a method for making such a test include compressing the sample repetitively by means of a dropped weight. The weight includes a plunger which moves vertically in a sliding bearing arrangement. The plunger is raised by a solenoid and allowed to drop so as to compress the sample only by a predetermined percentage of its original diameter. The force applied to the sample is monitored during this compression operation and the ratios of forces between the initial force measurement and the force measurement made during subsequent drops provides a quantitative indication of the weakness in the foam cell structure.

20 Claims, 5 Drawing Figures

TEST DEVICE AND METHOD FOR TESTING
FOAM MATERIAL

BACKGROUND OF THE INVENTION

The present invention relates to a test device and method and, more particularly, to a device and method suitable for testing a sample of foam material to detect weakness in the foam cell structure.

Foam material is used in many applications, such as those requiring thermal insulation or mechanical cushioning. Commonly, a foam material, such as a low density, lightly crosslinked, expanded polystyrene foam may be produced in the form of generally spherical beads which are on the order of ¼ inch in diameter. The polystyrene foam defines a gas tight cell structure of low density. It is desired that such foams exhibit a high fatigue resistance. This is the result of cell wall structures which remain intact through repeated deformation of the foam material.

A number of factors affect the strength and integrity of the foam cell walls and thus affect the gas tightness of the foam and its fatigue resistance. These factors include the polymer recipe, the blowing agent recipe and loading, the crazing agents used, and the polymer and foam residence time and temperature histories. In order to be able to adjust these factors to produce the best foam properties, it is necessary to test samples of materials in which the various factors have been varied, and to quantify the fatigue resistance of each sample.

In the past, testing of foam bead samples has been accomplished utilizing laboratory equipment which compressed the samples fairly slowly to a specified percentage of their original dimensions and measured the forces required to effect this compression. Typically such equipment has been powered by a servomotor, by a pneumatic arrangement, or by a hydraulic arrangement, and had effected compression of the sample typically at the rate of approximately 1 centimeter per second. Such test devices have been found not to be as sensitive as desired in distinguishing between various samples of foam material and, further, such test devices have been found to be relatively slow to operate.

Accordingly, it is seen that there is a need for an improved device and method for testing a sample of foam material with high sensitivity and in a rapid fashion.

SUMMARY OF THE INVENTION

This need is met a device which tests a sample of foam material to detect weakness in foam cell structure and which includes a support stand defining a sample support surface, and means for compressing a sample of foam material. The means for compressing the sample includes a plunger and a sliding bearing, the bearing being secured to the support stand and engaging the plunger, permitting vertical movement of the plunger. A means is provided for raising the plunger above the support surface and then causing the plunger to drop toward the support surface. A limit means limits the movement of the plunger toward the sample support surface, such that a sample may be compressed to a precise selected dimension by the plunger. A force measuring means detects the peak force applied to the sample during the compression of the sample by the plunger to the precise selected dimension.

The sliding bearing includes a striker plate on its upper surface. The limit means includes adjustable stop means for contacting the striker plate as the plunger drops so as to limit the downward travel of the plunger. The adjustable stop means may comprise a pair of stop nuts secured to an upper, threaded portion of the plunger. The force measuring means may be mounted on the bottom of the plunger such that a sample of foam material may be compressed between the force measuring means and the sample support surface. The force measuring means may comprise a quartz, piezoelectric force transducer.

A position indicator means is mounted on the support stand and operatively connected to the means for compressing a sample of foam material. The position indicator means provides an indication of the position of the plunger and the amount of compression of the sample of foam material. The position indicator means may comprise a linear voltage differential transformer having a coil assembly mounted on the support stand and a core which is vertically movable within the coil assembly. The coil is coupled between the means for raising the plunger and the plunger.

The means for raising the plunger may comprise a solenoid device which raises the plunger when energized and permits the plunger to fall freely when deenergized.

The device may further include control circuit means for controlling operation of the means for raising the plunger, such that the plunger is dropped a selected number of times to compress a sample of foam material, with the sample being compressed for a selected length of time after each drop of the plunger. The plunger is held in its raised position for a selected length of time prior to each such drop.

The device may comprise means for displaying and storing the output from the linear voltage differential transformer to provide an indication of the movement of the plunger. The device may further include means for storing and displaying the output from the force measuring means, including the peak force reached during each downward movement of the plunger.

A method of testing a sample of foam material to detect weakness in foam cell structure comprises the steps of:

(a) placing a foam bead of known diameter, $D_i$, on a support surface, (b) crushing the foam bead to a thickness equal to a selected percentage of $D_i$ by means of a dropped weight, (c) measuring the force exerted on the bead by the weight to crush the bead to the selected percentage of $D_i$, and (d) repeating the steps (b) and (c) a selected number of times.

The step (b) may include the step of crushing the foam bead for a preselected period of time. The step (d) may include the step of waiting a selected period of time prior to each repetition of steps (b) and (c).

Accordingly, it is an object of the present invention to provide a device and method for testing a sample of foam material to detect weakness in foam cell structure which performs the test quickly and with heightened sensitivity; to provide such a device and method in which the sample of foam material is repetitively crushed and the force required measured; and to provide such a device and method in which the downward movement of the weight is monitored.

Other objects and advantages of the invention will be apparent from the following description, the accompanying drawings and the appended claims.

DETAILED DESCRIPTION OF THE PREFERRED EMBODIMENT

Figure 1:
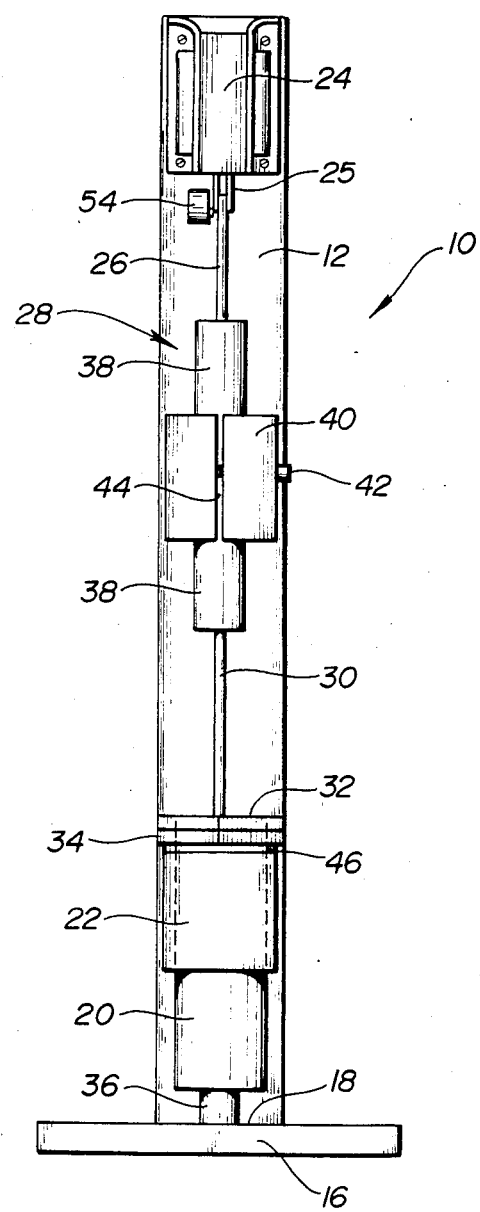
FIG. 1 is a front view of a device for testing a sample of foam material to detect weakness in foam cell structure, constructed according to the present invention.
Figure 2:
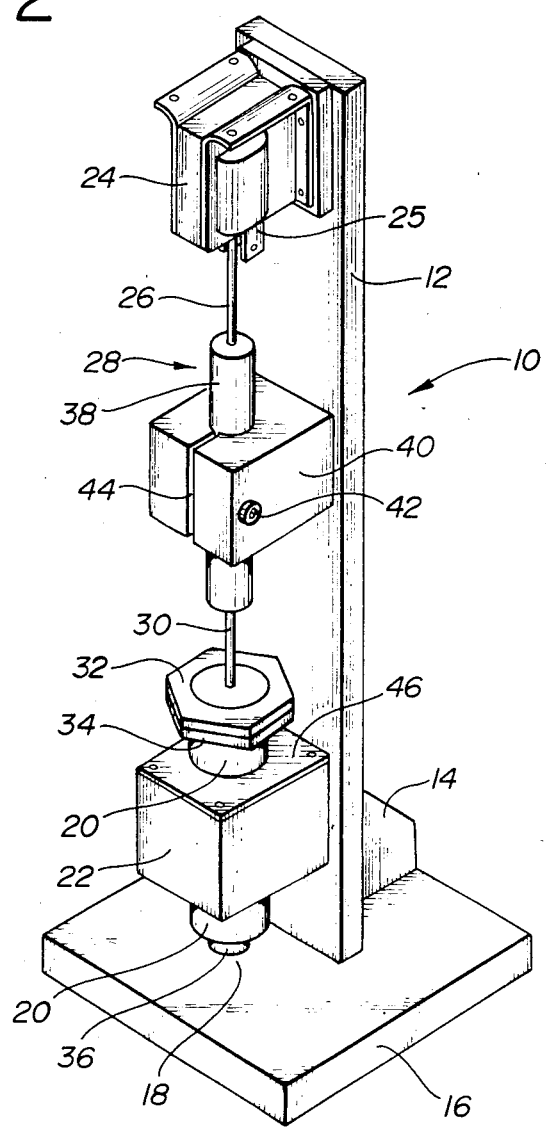
FIG. 2 is a perspective view of the device of FIG. 1.

Reference is made to FIGS. 1 and 2 which illustrate a device for testing a sample of foam material to detect weakness in foam cell structure, constructed according to the present invention. The device includes a support stand 10 having a back plate 12, a brace 14 and a base plate 16 which defines a sample support surface 18. A means for compressing a sample of foam mateial, preferably configured as a foam bead approximately ¼ inch in diameter, includes a plunger 20 and a sliding bearing 22. The bearing 22 is secured to the back plate 12 of the support stand 10 and engages the plunger 20 to permit free vertical movement thereof. Preferably, the plunger 20 is a highly polished cylinder of stainless steel which is vertically movably within a cylindrical opening in the bearing 22. Bearing 22 is lined with glass-filled teflon to facilitate unhampered vertical movement of the plunger 20.

A means for raising the plunger 20 above the support surface 18 and then releasing the plunger 20 to permit it to fall toward the support surface includes a solenoid device 24, having a solenoid plunger 25, attached to rod 26. Rod 26 is attached to the core (not shown) of linear voltage differential transformer 28, the opposite end of which is attached to the plunger 20 by means of rod 30. Thus, energization of the solenoid 24 results in the plunger 20 being raised, whereas deenergization of the solenoid 24 permits the plunger 20 to fall toward a sample of the foam material resting on the surface 18. The solenoid 24 may for example be a Model No. 14AC solenoid available from Guardian Electric Manufacturing Co., Chicago, Illinois.

A limit means, including a pair of stop nuts 32 and 34 secured to an upper threaded portion of the plunger 20, limits the downward movement of the plunger 20 toward the sample support surface such that a sample may be compressed to a precise dimension by te plunger 20. A force measuring means, such as quartz, piezoelectric force transducer 36 secured to the bottom of plunger 20 detects the peak force applied to the sample during the compression of the sample by the plunger 20, and provides an electrical force measurement signal in response thereto. The transducer 36 may preferably be a Model 208 transducer available from PCB Piezoelectronics, Inc., Buffalo, New York.

The linear voltage differential transformer 28 acts as a position indicator means for providing an indication of the position of the plunger 20 and the amount of compression of the sample of foam material. The linear voltage differential transformer 28 has a coil assembly 38 held by a bracket 40 on the back plate 12. The coil assembly 38 is secured within a cylindrical opening in the clamp 40 by bolt 42 which, when tightened, narrows slot 44 so as to clamp the coil assembly in the desired location. The linear voltage differential transformer may for example may be a Model No. 500HR transformer, available from Schaevitz Engineering, Pennsauken, New Jersey. As is known, such a device has a core which is freely movable within the coil assembly so as to couple magnetic flux produced by sensor current supplied to one coil to others of the coils in the coil assembly. The amount of flux coupled to these coils and the currents generated therein are dependent upon the position of the core.

The sliding bearing 22 includes a striker plate 46 on its upper surface which is impacted by stop nut 34 as the plunger 20 drops downward so as to limit the downward travel of the plunger. The stop nuts 32 and 34 are secured to an upper, threaded portion of the plunger 20 and are thereby adjustable with respect to the plunger so as to vary the amount of compression of the test sample, as described more fully below.

The present invention tests a foam bead sample by dropping a weight onto the sample to effect a precise degree of compression at a relatively high compression rate. The weight consists of the plunger 20, the force transducer 36, the stop nuts 32 and 34, rods 26 and 30, the core of LVDT device 28 and solenoid plunger 25. The solenoid 24 lifts the weight so as to raise the plunger 20 and transducer 36 above the surface 18 of base plate 16. A foam specimen is placed on the base plate 16 under the transducer 36. The stop nuts are then adjusted to yield a stroke which will crush the foam specimen to the desired degree. It has been found that significant data can be obtained by measuring the initial diameter $D_i$, and then crushing the test sample to a thickness of .10 $D_i$.

Under the command of the control circuit 48 (FIG. 4) the solenoid drops the plunger. A force measurement signal is produced by transducer 36 and amplified by preamp 50. The preamp 50 may, for example be a Model 434. A voltage amplifier available from PCB Piezoelectronics, Inc., Buffalo, New York. A peak detector circuit 52, which may preferably be a Model AP 4570 Track & Hold Module, available from action Instruments Co., Inc., San Diego, California, previously enabled by microswitch 54 as the plunger 20 begins its fall, detects the peak force reached during the crushing operation. This is displayed and stored by circuit 55.

Demodulator circuit 56 receives an output from transformer 28 and supplies a position signal to circuit 58 for display and storage, indicating the downward movement of the plunger 20 and the limit of downward movement of the plunger. Circuit 56 may preferably be a Model LPM-210 signal conditioning module variable from Schaevitz Engineering, Pennsauken, New Jersey.

This crushing operation is repeated a predetermined number of times and the fatigue resistance of the sample of foam material is quantified. Since instantaneous values of force and position are available, the stress/strain characteristics of the sample may be determined under the relatively high compression rates produced by the dropped weight.

Figure 3:
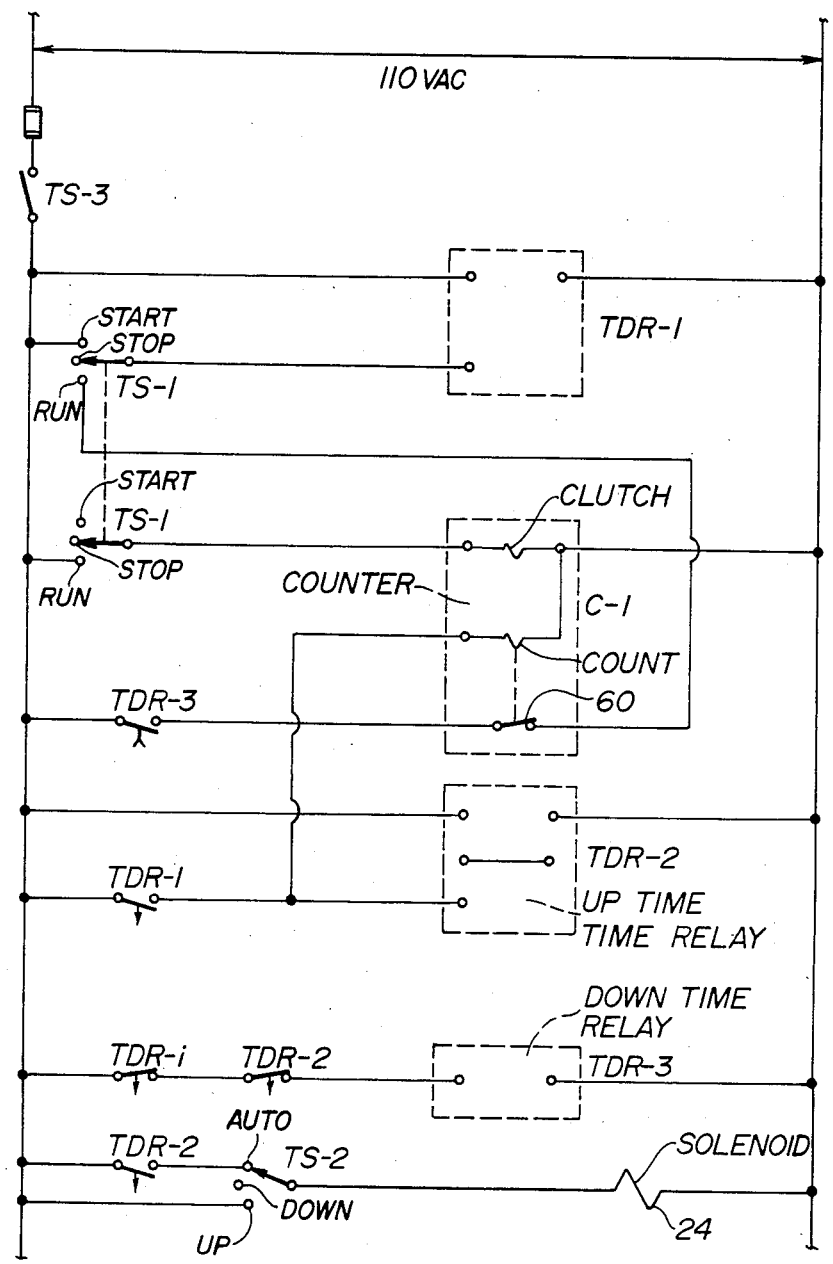
FIG. 3 is an electrical schematic diagram illustrating the control circuit according to the present invention.
Figure 4:
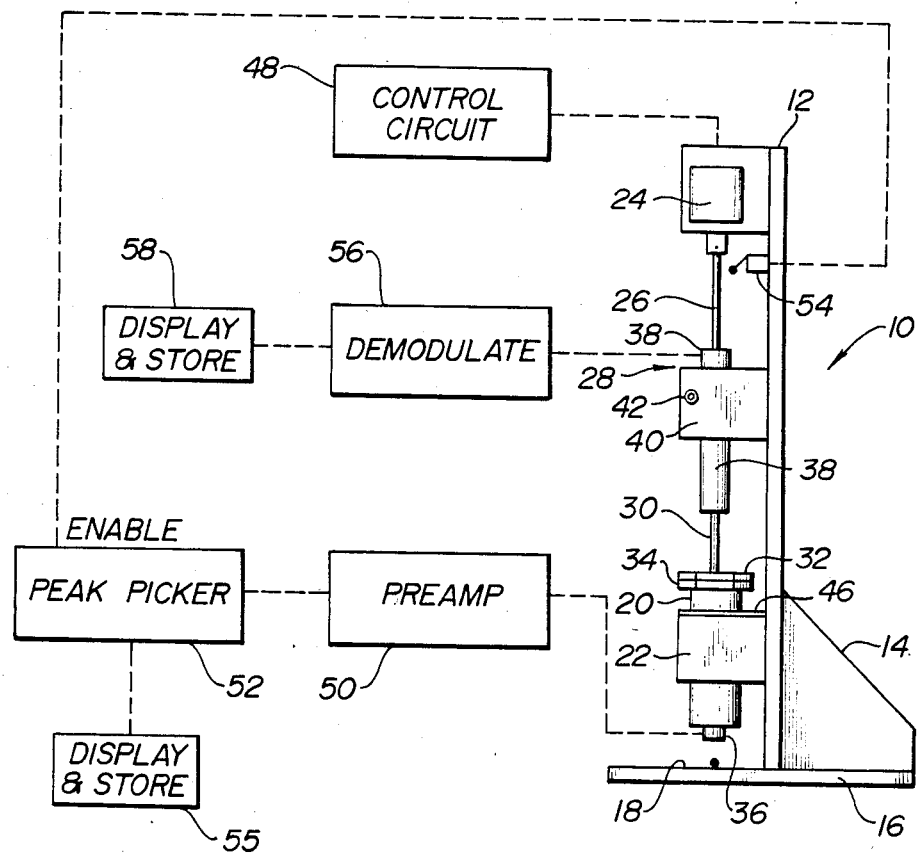
FIG. 4 is a diagrammatic view of the device of FIG. 1, illustrating the circuitry which monitors and displays movement of the plunger and force applied to the test sample.

Reference is made to FIG. 3 which illustrates the control circuit 48 of FIG. 4 in greater detail. The circuit uses three time delay relays, TDR-1, TDR-2, and TDR-3, which preferably may be ATC 328-A adjustable time delay relays available from Automatic Timing & Controls Co., King of Prussia, Pennsylvania, and a GW HZ107A600 electromechanical counter C-1, available from GW Eagle Signal Industrial Controls, to energize and deenergize the solenoid 24. The relay TDR-1 is a reset timer which is set to time out at approximately 50 milliseconds. The relay TDR-2 controls the length of time during which the plunger is raised, whereas the relay TDR-3 controls the length of time during which the plunger remains down, compressing the sample. The counter C-1 is a count-down counter which is set for the desired number of impacts. Deenergizing the clutch coil automatically resets the counter C-1. When the count which has been selected is reached, the counter switch 60 is opened, interrupting the supply of current to relay TDR-1, and terminating the test operation.

At the initiation of operation, the switch TS-1 is switched to its start position, causing the plunger to be raised. Then the switch TS-1 is switched into the "run" position. After timing out of the relay TDR-2, the plunger 20 drops, compressing the sample, and remaining down for a period of time determined by relay TDR-3. Thus the control circuit includes a means for raising and dropping the plunger a selected number of times, with the sample being compressed for a selected length of time after each drop of the plunger, and with the plunger being held in its raised position for a selected length of time prior to each such drop.

As discussed previously, optimum foam material has cell walls which remain intact through repeated crushing cycles, resulting in consistent peak force values being measured by the test device. Poor foam material, however, ruptures some or all of its cell walls on successive impacts, yielding a series of declining peak force values. One technique for producing repeatable, quantitative results from experimental data obtained in this fashion is to calculate a dimensionless ratio, comparing a test sample's peak force on the first impact to its peak force on a subsequent impact. It has been found that foam materials of varying composition may be effectively compared quantitatively in this manner. Further, it has been found that the present invention provides an approach to testing foam materials which is more sensitive in distinguishing foam material quality than with prior art approaches.

Figure 5:
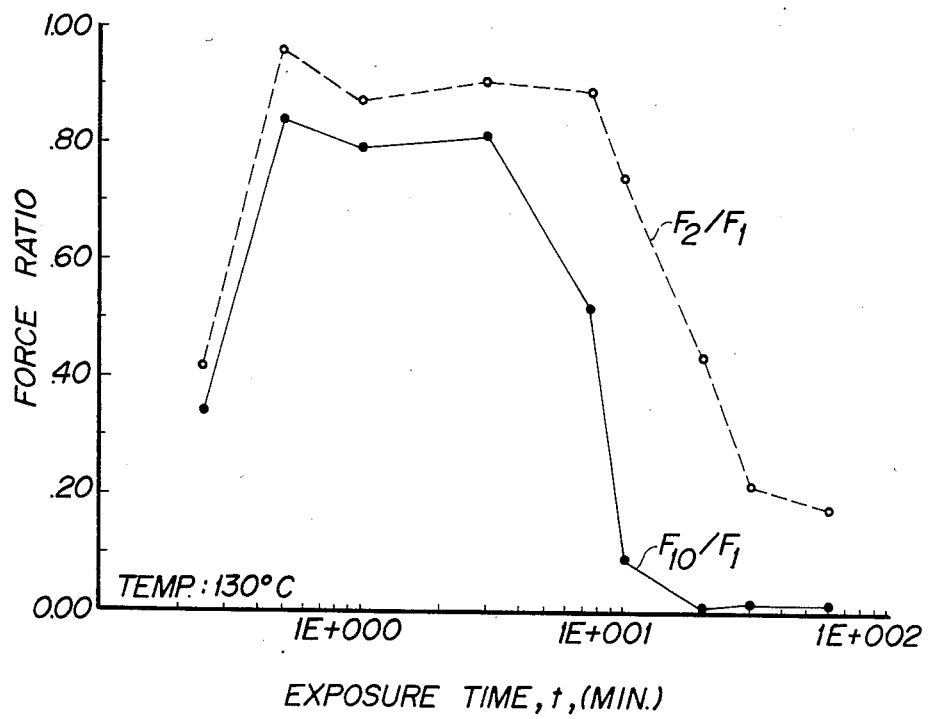
FIG. 5 is a graph which is useful in understanding the present invention.

Reference is made to FIG. 5 which illustrates the improved performance of a test device according to the present invention. The dashed line indicates initial strength ratios (ratio of peak forces on the first and second impacts), whereas the solid line indicates the ultimate strength ratios (ratio of peak forces on the first and tenth impacts). The graphs portray data taken to determine the effect of varying the exposure time at 130° C. during foaming. Note that the peak of foam performance in the exposure time range of 1–3 minutes is clearly detected by the device of the present invention. The greater loading rate produced by this device is apparently responsible for this high sensitivity. Actually, the loading rate to which a sample is subjected by a device according to the present invention is in the range of 50 to 100 cm./sec., depending on the stroke of the plunger 20, whereas prior art load rates are less than 20 cm./sec. and usually on the order of 1 cm./sec.

Having described the invention in detail and by reference to preferred embodiments thereof, it will be apparent that modifications and variations are possible without departing from the scope of the invention defined in the appended claims.

What is claimed is:

1. A device for testing a sample of foam material to detect weakness in foam cell structure, comprising:
   a support stand defining a sample support surface,
   means for compressing a sample of foam material, said means including a plunger and a sliding bearing, said bearing being secured to said support stand and engaging said plunger to permit vertical movement thereof,
   means for raising said plunger above said support surface and then causing said plunger to drop toward said support surface,
   limit means for limiting the movement of said plunger toward said sample support surface, such that a sample may be compressed to a precise dimension by said plunger, and
   force measuring means for detecting the peak force applied to said sample during the compression of said sample to said precise dimension by said plunger.

2. The device of claim 1, further comprising
   position indicator means, mounted on said support stand and operatively connected to said means for compressing a sample of foam material, for providing an indication of the position of said plunger and the amount of compression of said sample of foam material.

3. The device of claim 2 in which said position indicator means comprises a linear voltage differential transformer having a coil assembly mounted on said support stand and a core which is vertically movable within said coil assembly, said core being attached to said means for raising said plunger and said plunger.

4. The device of claim 3 further comprising means for displaying and storing the output from said linear voltage differential transformer to provide an indication of the movement of said plunger.

5. The device of claim 1 in which said means for raising said plunger comprises a solenoid device.

6. The device of claim 5, in which said solenoid device raises said plunger when energized and permits said plunger to fall freely when deenergized.

7. The device of claim 1 in which said sliding bearing includes a striker plate on its upper surface, and in which said limit means includes adjustable stop means for contacting said striker plate as said plunger drops so as to limit the downward travel of said plunger.

8. The device of claim 7 in which said adjustable stop means comprises a pair of stop nuts secured to an upper, threaded portion of said plunger, said stop nuts being adjustable with respect to said plunger so as to limit the downward motion of said plunger.

9. The device of claim 1, in which said force measuring means is mounted on the bottom of said plunger such that a sample of foam material to be tested is compressed between said force measuring means and said sample support surface.

10. The device of claim 9 in which said force measuring means comprises a quartz, piezoelectric force transducer.

11. The device of claim 1, further comprising control circuit means for controlling operation of said means for raising said plunger such that said plunger is dropped a selected number of times, to compress a sample of foam material with the sample being compressed for a selected length of time after each drop of said plunger, and with the plunger being held in its raised position for a selected length of time prior to each such drop.

12. The device of claim 1 further comprising means for storing and displaying the output from said force measuring means, including the peak force reached during each downward movement of the plunger.

13. A method of testing a sample of foam material to detect weakness in foam cell structure, comprising the steps of:
    (a) placing a foam bead of known diameter, $D_i$, on a support surface,
    (b) crushing said foam bead to a thickness equal to a selected percentage of $D_i$ by means of a dropped weight,
    (c) measuring the force exerted on said bead by said weight to crush said bead to said selected percentage of $D_i$, and
    (d) repeating said steps (b) and (c) a selected number of times.

14. The method of claim 13 in which said step (b) includes the step of crushing said foam bead for a preselected period of time.

15. The method of claim 13 in which said step (d) comprises the step of waiting a selected period of time prior to each repetition of steps (b) and (c).

16. A device for testing of sample of foam material to detect weakness in foam cell structure, comprising:
    a plunger element,
    means for guiding said plunger element in a generally vertical path above a sample,
    means for raising said plunger element and, thereafter, allowing said plunger element to fall such that it compresses the sample of foam material,
    means for limiting the travel of said plunger toward said sample, such that a sample may be compressed to a precise dimension by said plunger, and
    means for measuring the force applied to the sample of foam material as it is compressed.

17. The device of claim 16 in which said means for measuring the force applied to the sample of foam material as it is compressed comprises means for detecting and storing the maximum force exerted on the sample during compression.

18. The device of claim 17, further comprising means for displaying the maximum force exerted on the sample during compression.

19. The device of claim 16, further comprising means for measuring the downward movement of said plunger element.

20. The device of claim 19 further comprising means for displaying the downward movement of said plunger element.

* * * * *

UNITED STATES PATENT AND TRADEMARK OFFICE
CERTIFICATE OF CORRECTION

PATENT NO. : 4,649,735

DATED : March 17, 1987

INVENTOR(S) : Roger K. Pihlaja

It is certified that error appears in the above-identified patent and that said Letters Patent is hereby corrected as shown below:

Column 2, line 45, "$D_1,$" should read --$D_i,$--.

Signed and Sealed this

Eighth Day of September, 1987

Attest:

DONALD J. QUIGG

Attesting Officer

Commissioner of Patents and Trademarks